(12) United States Patent
Sirringhaus

(10) Patent No.: US 8,080,152 B2
(45) Date of Patent: Dec. 20, 2011

(54) EMBOSSING OF MICROFLUIDIC SENSORS

(75) Inventor: Henning Sirringhaus, Cambridge (GB)

(73) Assignee: Cambridge Enterprise Ltd., Cambridge (GB)

( * ) Notice: Subject to any disclaimer, the term of this patent is extended or adjusted under 35 U.S.C. 154(b) by 1191 days.

(21) Appl. No.: 10/549,329

(22) PCT Filed: Mar. 17, 2004

(86) PCT No.: PCT/GB2004/001135
§ 371 (c)(1),
(2), (4) Date: Jul. 24, 2006

(87) PCT Pub. No.: WO2004/083843
PCT Pub. Date: Sep. 30, 2004

(65) Prior Publication Data
US 2006/0272942 A1  Dec. 7, 2006

(30) Foreign Application Priority Data

Mar. 18, 2003 (GB) .................................. 0306163.7

(51) Int. Cl.
*G01N 27/414* (2006.01)
(52) U.S. Cl. .................. 205/775; 204/400; 204/403.01; 264/293; 257/253
(58) Field of Classification Search .................. 204/400, 204/406, 403.01, 409, 416, 433; 264/284, 264/293; 257/253
See application file for complete search history.

(56) References Cited

U.S. PATENT DOCUMENTS

| | | | | |
|---|---|---|---|---|
| 5,194,133 A | * | 3/1993 | Clark et al. | 204/608 |
| 5,250,168 A | * | 10/1993 | Tsukada et al. | 204/416 |
| 5,384,028 A | * | 1/1995 | Ito | 257/253 |
| 5,393,401 A | * | 2/1995 | Knoll | 204/403.06 |
| 5,405,511 A | * | 4/1995 | White et al. | 205/777.5 |
| 6,321,791 B1 | * | 11/2001 | Chow | 137/833 |
| 6,676,815 B1 | * | 1/2004 | Bhullar et al. | 204/403.03 |
| 6,730,212 B1 | * | 5/2004 | Yamagishi et al. | 205/777.5 |
| 6,890,715 B1 | * | 5/2005 | Lewis et al. | 435/6 |

FOREIGN PATENT DOCUMENTS

| | | |
|---|---|---|
| EP | 0 398 587 A2 | 11/1990 |
| EP | 0 633 468 A2 | 1/1995 |
| EP | 0 668 500 A2 | 8/1995 |
| WO | WO 02/29912 A1 | 4/2002 |
| WO | WO 02/086162 A1 | 10/2002 |

OTHER PUBLICATIONS

W.H. Baumann, et al, "Microelectronic Sensor System for Microphysiological Application on Living Cells", Sensors and Actuators B, vol. 55, No. 1, Apr. 25, 1999, pp. 77-89.
Joel S. Rossier, et al, "Enzyme Linked Immunosorbent Assay on a Microchip With Electrochemical Detection", Lab on a Chip, Royal Society of Chemistry, Cambridge, GB, vol. 1, No. 2, Dec. 2001, pp. 153-157, XP009030699.

\* cited by examiner

*Primary Examiner* — Kaj K Olsen
(74) *Attorney, Agent, or Firm* — Sughrue Mion, PLLC

(57) ABSTRACT

An electrochemical sensor and method of its production comprising a microfluidic channel and an electronic sensing device on a first substrate, and a second substrate bonded to the first substrate so as to close the microfluidic channel, wherein a functional part of the electronic sensing device is exposed at the surface of the microfluidic channel and wherein the microfluidic channel is formed by embossing. In one embodiment the electronic device is a vertical-channel field-effect transistor.

14 Claims, 8 Drawing Sheets

(A)

(B)

(A)

(B)

EMBOSSING OF MICROFLUIDIC SENSORS

This application is a 371 National Stage Entry of PCT/GB2004/001135 filed on Mar. 17, 2004.

This invention relates to organic electronic devices and the use of such devices as sensors.

BACKGROUND OF THE INVENTION

Semiconducting conjugated polymer thin-film transistors (TFTs) or more generally field-effect transistors (FETs) have recently become of interest for applications in cheap, logic circuits integrated on plastic substrates (C. Drury, et al., APL 73, 108 (1998)) and optoelectronic integrated devices and pixel transistor switches in high-resolution active-matrix displays (H. Sirringhaus, et al., Science 280, 1741 (1998), A. Dodabalapur, et al. Appl. Phys. Lett. 73, 142 (1998)). In test device configurations with a polymer semiconductor and inorganic metal electrodes and gate dielectric layers high-performance TFTs have been demonstrated. Charge carrier mobilities up to 0.1 $cm^2$/Vs and ON-OFF current ratios of $10^6$-$10^8$ have been reached, which is comparable to the performance of amorphous silicon TFTs (H. Sirringhaus, et al., Advances in Solid State Physics 39, 101 (1999)).

One of the advantages of polymer semiconductors is that they lend themselves to simple and low-cost solution processing. However, fabrication of all-polymer TFT devices and integrated circuits requires the ability to form lateral patterns of polymer conductors, semiconductors and insulators. Various patterning technologies such as photolithography (WO 99/10939 A2), screen printing (Z. Bao, et al., Chem. Mat. 9, 1299 (1997)), soft lithographic stamping (J. A. Rogers, Appl. Phys. Lett. 75, 1010 (1999)) and micromoulding (J. A. Rogers, Appl. Phys. Lett. 72, 2716 (1998)), as well as direct ink-jet printing (H. Sirringhaus, et al., UK 0009911.9) have been demonstrated.

Many direct printing techniques are unable to provide the patterning resolution that is required to define the source and drain electrodes of a TFT. In order to obtain adequate drive current and switching speed channel lengths of less than 10 µm are required. In the case of inkjet printing this resolution problem has been overcome by printing onto a prepatterned substrate containing regions of different surface free energy (H. Sirringhaus et al., UK 0009915.0).

In WO0229912 and UK 0229191.2 methods are described for the fabrication of organic TFTs by embossing. The methods are based on forming a microgroove by embossing a rigid master into a substrate, and forming a field-effect device inside the embossed microgroove. The substrate can be a flexible deformable plastic substrate, a rigid substrate containing a flexible overlayer, or even a rigid substrate in the case of melt embossing. Planar-channel and vertical-channel field-effect devices with short, submicrometer channel lengths can be fabricated in this way. The embossing step is an integral part of the device manufacturing process. Microcutting is used to define the critical-feature channel length between source- and drain-electrodes of planar-channel and vertical-channel devices. The topographic profile of the embossed grooves is used to pattern the surface energy of the substrate in order to confine the deposition of an ink solution to a defined area on the substrate. An example is a self-aligned gate electrode, where the conducting ink for deposition of the conductive gate electrode is confined to the embossed grooves with the help of selective surface modification that makes the flat regions of the substrate repulsive for the deposition of the ink.

One important application of organic FETs are in sensors, such as, but not limited to, sensors of chemical, biological, or gaseous species, or temperature or humidity sensors. The sensing ability of the FET is based on some change in the electrical characteristics of the FET when exposed to an environment that contains a small concentration of the species to be detected (or upon temperature/humidity change). A range of different FET device configurations can be used for this purpose. In a chemical FET (CHEMFET) the gate electrode is formed from a material that interacts with the species to be detected, the interaction affecting the gate voltage. An example of a conventional, inorganic CHEMFET is a silicon MOSFET with a Pd gate for the detection of $H_2$ hydrogen gas. At elevated temperatures, the hydrogen is thought to dissolve into the Pd gate, diffusing to the Pd/$SiO_2$ interface and forming an electrical layer that affects the flat band voltage of the metal-oxide-semiconductor (MOS) structure, and shifts the threshold voltage of the FET. For given applied source, drain, and gate voltages this shift of threshold voltage results in a change of the source-drain current.

Some of the key requirements for a good FET sensor are:
Selectivity: The sensor should ideally react only to the species or environmental factor that it is meant to detect, and not be equally sensitive to the presence of other species. This requirement can be difficult to achieve, but can, for example, be relaxed by using an array of different sensors each with different sensitivities to the various different species that the sensor array can potentially be exposed to during operation.
Sensitivity: The sensor should be highly sensitive to the presence of the species to be detected. The sensitivity is dependent on both the nature of the interaction between the species and the sensor, as well as on the geometry of the sensor determining the area of interaction. In the case of many FET sensors such as a CHEMFET the sensitivity of the sensor is determined by the transconductance of the FET, i.e. the change in source-drain current in response to a change in gate voltage.
Information processing: The signal from the sensing element needs to be in such a form that it can be easily processed into a form that can be transmitted to the information gathering unit. In the case of an FET sensor this means that the current or voltage signal supplied by the FET upon detection of the species is sufficiently large to allow signal processing.
Linearty: The response of the sensor to the species to be detected should be approximately linearly dependent on the concentration of the species, in order to facilitate the calibration of the sensor.
Stability: The response of the sensor should be stable during its operation, i.e. it should always give the same response when exposed to the same concentration of species. If the response of the sensor changes in time, frequent recalibration is required which can be difficult, in particular in situations where the sensor is not easily accessible.

In many sensor applications the sensor needs to be exposed to a stream of liquid or gas containing the species to be detected. The concentration of the species can be small, requiring a large area of interaction exposed to the flow of liquid gas. In particular, for biological sensors the volumes of liquid that contain, for example, an enzyme to be detected can be small, and sensor configuration need to be used in which the probability that the species comes in contact with the sensor, as the flow is passing by, is maximised.

Controlling the flow of liquids by using microfabricated channels ("microfluidics") is a field with a growing number of applications. A common technique is to form a network of microfluidic channels in an elastomer sample, such as poly (dimethylsiloxane) (PDMS). The PDMS is poured over a master containing a topographic profile, that can be fabricated by techniques, such as photolithography, curing the elastomer, and removing it from the master. The PDMS sample then contains an array of recessed channels. These channels can be sealed by bonding the PDMS to a flat substrate, such as a glass substrate or another flat PDMS sample. Often an oxygen plasma treatment is used to improve the adhesion between the two substrates, which is important to seal the channels against leakage of liquid. Examples of applications of such microfluidic channels are the patterned delivery and deposition of biomolecules on surfaces (E. Delamarche et al., Science 276, 779 (1997)), the localized reaction between two species inside a microfluidic channel followed by deposition on the substrate (P. Kenis et al., Science 285, 83 (1999)), the realization of a large number of reaction chambers the contents of which can be individually controlled (T. Thorsen, et al., Science 298, 580 (2002)). In principle, a microscopic version of a laboratory can be created in this way (lab-on-a-chip). Key components of such microfluidic system such as valves and pumps have been developed (M. Unger, Science 288, 113 (2000)). In all of these applications it would be highly desirable if a diagnostic tool in the form of a sensor could be integrated into the microfluidic channels in order to measure for example the concentration of reagents, or detect the presence of a reaction product.

BRIEF SUMMARY OF THE INVENTION

The present invention discloses an FET sensor that can be integrated into a microfluidic channel. The fabrication of an FET device inside a microgroove on a first substrate, such as that shown in FIG. 6, is disclosed herein. The microgrooves can be sealed by bonding the first substrate to a second substrate. When liquid or gas is flowing through such a microfluidic channel, it comes in close contact with a surface of the sensing device, resulting in a high sensitivity of the sensor.

According to a first aspect of the present invention there is provided a sensor comprising a microfluidic channel and an electronic sensing device on a first substrate, and a second substrate bonded to the first substrate so as to close the microfluidic channel, wherein a functional part of the electronic sensing device is exposed at the surface of the microfluidic channel.

The exposed functional part of the electronic sensing device may be organic, and may be a polymer.

The microfluidic channel could suitably be formed by embossing.

The exposed functional part of the electronic sensing device could be insoluble in water. The functional part is preferably a part on whose properties the electrical characteristics of the device are dependent. An electrical property of the exposed functional part could be sensitive to environmental conditions within the channel, such as temperature or the presence of a species to be sensed.

The electronic sensing device could suitably be a transistor. The exposed functional part of the electronic sensing device could be an insulating layer, and could be a gate dielectric of the transistor, or it could be a conducting layer, in which case it could be a gate electrode of the transistor. Alternatively, the exposed functional part could be a semiconducting layer, and could be an active semiconducting layer of the transistor.

The height of the channel is preferably 1 mm or less, and most preferably 20 µm or less. The width of the channel is preferably 1 mm or less, and most preferably 20 µm or less.

The transistor may be a vertical-channel field-effect transistor.

According to a second aspect of the present invention there is provided a sensor comprising a first organic substrate having a microfluidic channel and an electronic sensing device located therein, and a second substrate bonded to the first substrate so as to close the microfluidic channel.

The second substrate could be an elastomer, and a further microfluidic channel could suitably be located in the second substrate. A conducting part of the sensing device could be exposed at the surface of the microfluidic channel, and the conducting part could suitably be organic, and in particular PEDOT/PSS. The sensor could suitably be for sensing the presence of glucose in the microfluidic channel, or for detecting the pH level of a substance in the microfluidic channel.

According to a third aspect of the present invention there is provided a sensor comprising a microfluidic channel and a pair of electrodes of an electronic sensing device, wherein the microfluidic channel and the pair of electrodes are defined in a single operation.

The single operation could suitably be embossing. The microfluidic channel could be located in an organic substrate. Current flowing between the electrodes is suitably sensitive to environmental conditions within the channel, and the environmental conditions could be temperature or the presence of a species to be sensed.

The electrodes could suitably form source and drain electrodes of a field-effect transistor, and the field-effect transistor could suitably be a vertical-channel field-effect transistor.

One or more electronic devices could suitably be integrated onto the first substrate of a sensor, and the other electronic devices could be electronically connected to the electronic sensing device. The other electronic sensing devices could perform signal amplification, memory or calibration functions.

According to a fourth aspect of the present invention there is provided a method for producing a sensor, the method comprising the steps of: forming a body comprising an electrically conductive layer; and embossing the body to define a microfluidic channel and a pair of electrodes, the pair of electrodes being exposed at the surface of the channel.

The step of defining the pair of electrodes could suitably comprise microcutting the electrically conductive layer. The method could further comprise a step of depositing over the body a layer of a semiconductive material, a step of depositing over the layer of semiconductive material a layer of an insulating material and a step of depositing over the layer of insulating material a layer of a conductive material.

According to a fifth aspect of the present invention there is provided a sensor comprising a microfluidic channel and an electronic sensing device, wherein an insulating part of the electronic sensing device is exposed at the surface of the microfluidic channel.

BRIEF DESCRIPTION OF THE DRAWINGS

The present invention will now be described by way of example, with reference to the accompanying drawings, in which.

DESCRIPTION OF THE EXEMPLARY EMBODIMENTS

Figure 1:
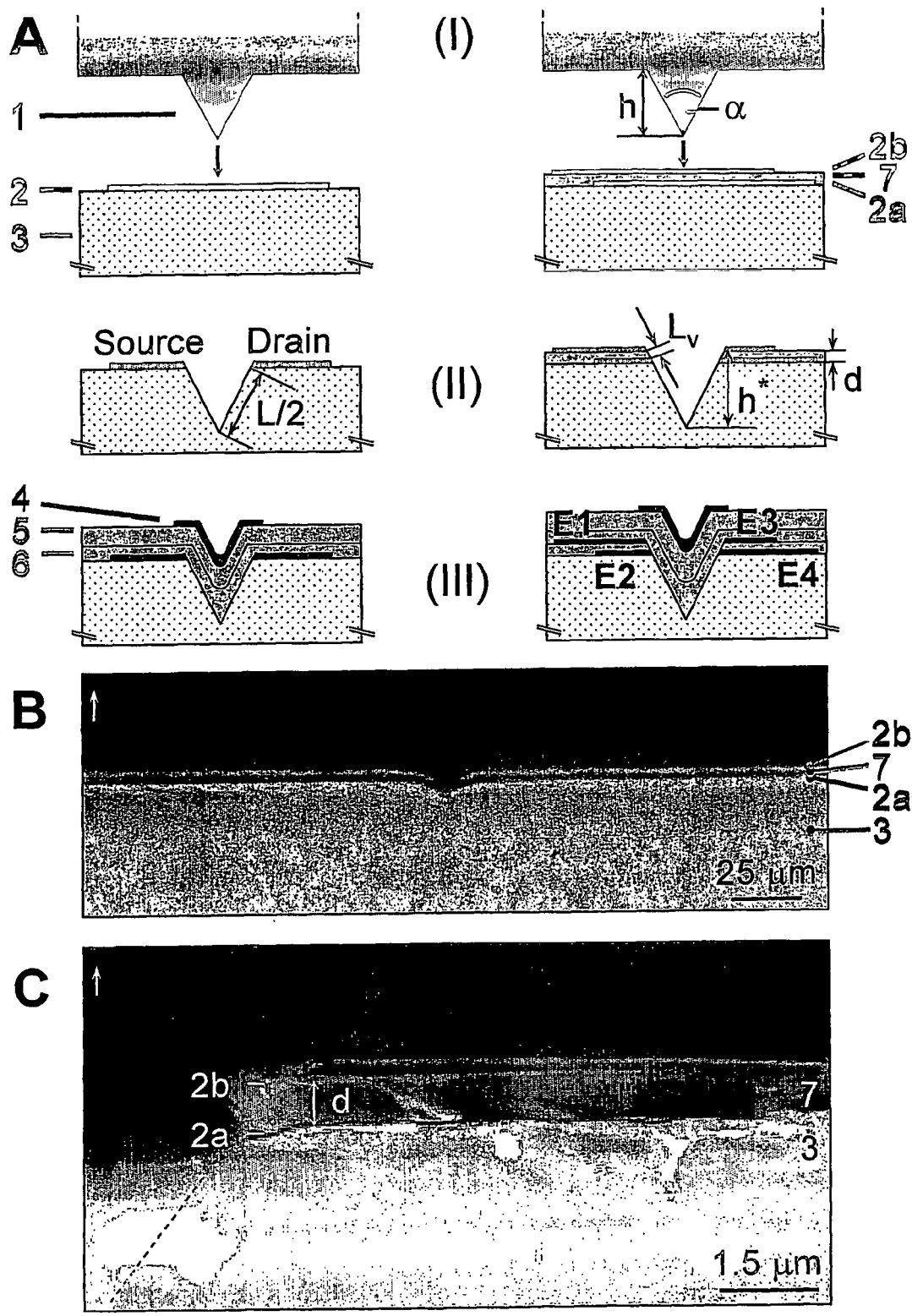
FIG. 1(A) is a schematic diagram of one embodiment of the solid state embossing and microcutting process to fabricate planar-channel and vertical-channel FET devices.
FIGS. 1(B) and 1(C) are environmental scanning electron microscopy images of a microcut FET channel.

As an example of one aspect of the present invention an architecture for an electronic sensing device is disclosed, where the electronic sensing device is located inside a microchannel that carries a flow of liquid or gas.

As an example of another aspect of the present invention a method is disclosed for forming an electronic sensing device located inside a microchannel that can carry a flow of liquid or gas, by embossing, wherein the embossing step defines in the same operation at least one part of the electronic sensing device and also at least one part of the microfluidic channel.

The invention will now be described in two parts, the first part focuses on the formation of the electronic sensing device, and the second part focuses on the formation of the microfluidic channel.

The electronic device that is formed inside the microgrooves on the first substrate needs to be configured in such a way that it is able to sense the presence of the species of interest. A large number of possible sensor configurations that can be integrated into the microgroove can be found from the literature in this field. Examples include, but are not limited to, chemically sensitive resistors, capacitors, diodes and transistors (see for example, Janata et al., Nature Materials 2, 19 (2003)). In all cases the device characteristics, and specifically its electrical properties, change upon exposure to the species of interest. In a chemical resistor, the conductivity of a conductive or semiconductive film in between two electrodes is dependent on the concentration of the species to be detected. In a chemical capacitor, the impedance characteristics, in particular the flat band voltage of a metal-semiconductor-insulator diode change/shift upon exposure to the species. In a chemical diode the height of the Schottky barrier at a metal-semiconductor junction depend on concentration. In a chemical transistor (CHEMFET) the threshold voltage of the FET shifts upon exposure to the species to be detected. The structure of a chemical capacitor is similar to that of a CHEMFET, in fact the detection mechanism in a CHEMFET might also be based on measurement of the gate to source/drain capacitance of impedance characteristics.

In one example of a CHEMFET the gate electrode is formed from a metal that allows diffusion of the species to be detected through the bulk of the gate metal to the interface with the gate dielectric. In the case of a hydrogen $H_2$ sensor a Pd gate can be for example. In another example, the sensing mechanism relies on variations of the workfunction of the metal gate electrode upon exposure to species to be detected resulting in a shift of the FET threshold voltage $V_T$. Alternatively, in a CHEMFET the detection mechanism might also be based on changes of the charge transporting properties of the active semiconducting layer upon exposure (B. Crone, et al. Appl. Phys. Lett. 78, 2229 (2001)).

According to one embodiment the source, drain and/or gate electrodes of a CHEMFET are defined by an embossing step, simultaneously generating a microgroove that can be used to define a flow channel for the analyte.

FIG. 1 illustrates the fabrication of both planar- and vertical-channel FETs that can be used as sensors by embossing according to one embodiment. A significant feature of a vertical-channel polymer FET is that the channel length can be defined by simple control of the thickness of a film, and not by a high-resolution submicrometer lithography step. This approach provides a low-cost manufacturing technique for submicrometer FETs based on solution processing and direct printing. In the context of sensing devices a useful feature of a short-channel submicrometer FET is that it provides a large transconductance. The transconductance of an FET scales inversely with the channel length, i.e. the shorter the channel the larger the current variation induced by a given change of the gate potential due to interaction with the species to be detected.

The process consists of forcing a microcutting tool comprising an array of sharp protruding wedges into a multilayer structure of one or more electrically conductive layers on a poly(ethylene-terephtalate) (PET) substrate. For the planar-channel FETs (FIG. 1A, left column), a single conducting layer for the source-drain electrodes is deposited on top of the substrate. Electrodes are coarse patterned by inkjet printing of the conducting polymer poly(3,4-ethylenedioxythiophene) doped with poly(styrene sulphonic acid) (PEDOT/PSS) or, alternatively, by shadow-mask evaporation of gold. During the microcutting, the substrate is held just below its glass transition temperature, $T_g$ (for PET of $T_g \approx 80°$ C., $T_{emboss} \approx 70$-$75°$ C.), and a nominal pressure of ~100 g mm$^{-2}$ is applied for 30-60 min, such that a V-shaped microgroove cuffing the metal layer is formed (FIG. 1A, left column). The embossing time can be shortened by using higher load pressure. Subsequently, layers of polymer semiconductor and gate insulator are deposited conformally into the microgroove by spin-coating. Swelling of underlying layers was avoided by judicious choice of solvents and processing parameters. Semiconducting poly(9,9-dioctylfluorene-co-bithiophene) (F8T2) or regioregular poly(3-hexylthiophene) were deposited from a 0.3 wt % (F8T2) and 0.7 wt % (P3HT) solution in m-xylene. The gate dielectric poly(vinyl phenol) (PVP) was deposited from a 10 wt % solution in isopropanol. Finally, a top-gate electrode was applied, either by shadow-mask evaporation of gold, or by self-aligned inkjet printing of PEDOT into the embossed groove as discussed below. The master comprised sharp, protruding wedges of height h~10 μm and periodic distance, Λ, between wedges of 500 μm producing 5 to 10 μm deep cuts (cf. optical micrograph in FIG. 1B) and planar channel length L≈12-17 μm.

As down-scaling of L, is highly desirable to improve switching speed, we set out to fabricate also vertical-channel FETs, in which the channel length is defined by the thickness of a deposited insulating polymer layer, rather than by the master geometry. (The term "vertical" refers to the conventional orientation of the device during fabrication, but the device could adopt and be fabricated in any orientation). First, a trilayer structure consisting of two coarse-patterned electrode layers, separated by a thin polymer insulator layer, is fabricated by depositing thin gold or PEDOT pads onto a PET substrate; spin-coating a 0.5-1 μm PVP layer from isopropanol; and applying another slightly shifted set of gold or PEDOT electrodes (FIG. 1A, right column). Subsequently, employing the same process parameters as above, the conductor/insulator/conductor triple-layer supported by the PET substrate was microcut. In this way source-drain electrodes for two submicron, vertical-channel FETs (E1-E2 and E3-E4) and two planar source-drain pairs (E1-E3 and E2-E4) are fabricated simultaneously. In FIG. 1C the thickness, d, of the PVP layer was measured to be 700 nm, leading to a channel length L≈900 nm. The vertical devices were completed as described for the planar devices above, using PMMA spin-coated from a 0.7 wt % solution in butyl acetate as gate dielectric.

Figure 2:
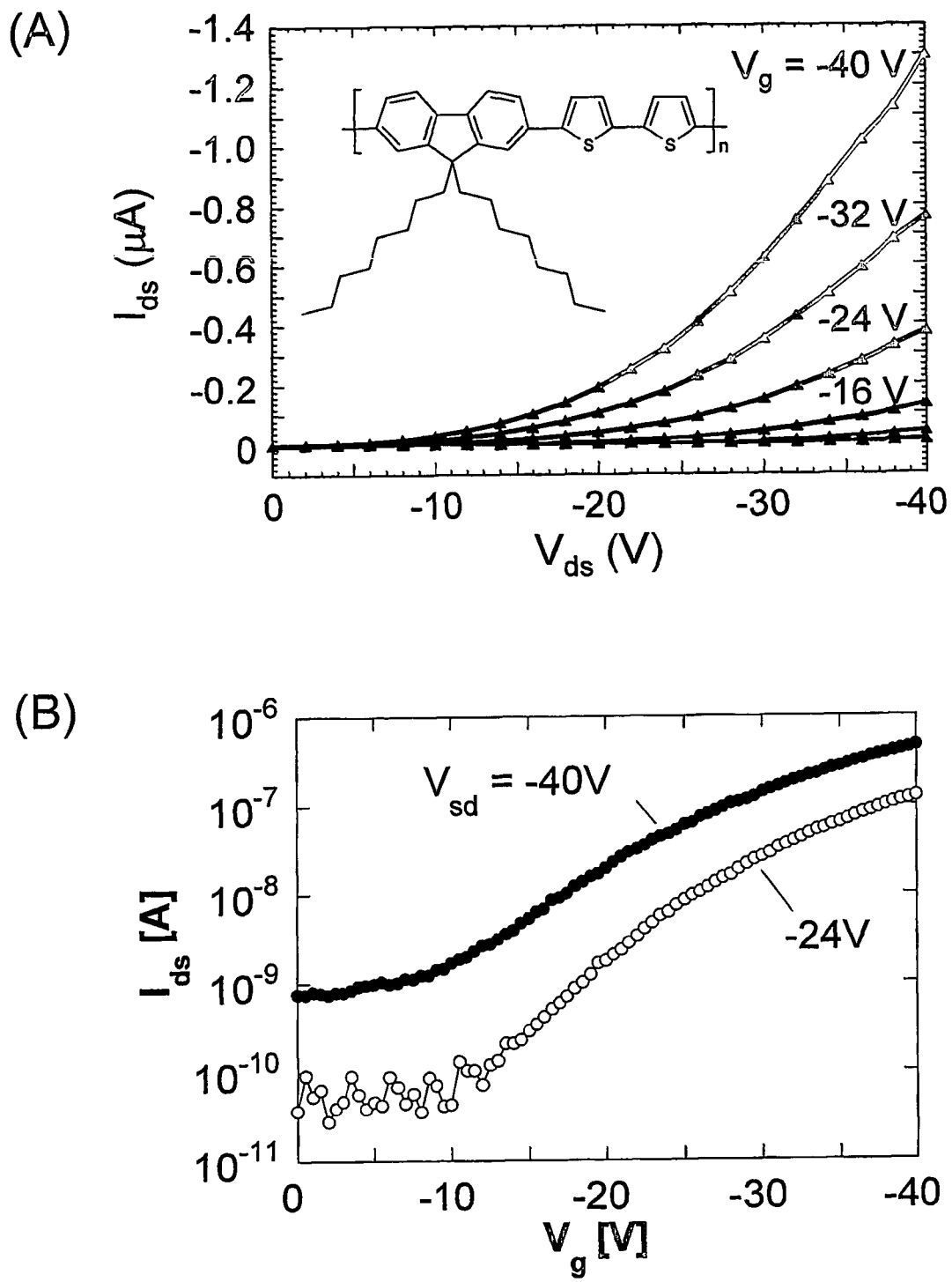
FIGS. 2A and 2B show output and transfer characteristics of an embossed vertical FET with a semiconducting polymer active layer of poly(dioctylfluorene-co-bithiophene) (F8T2)
Figure 3:
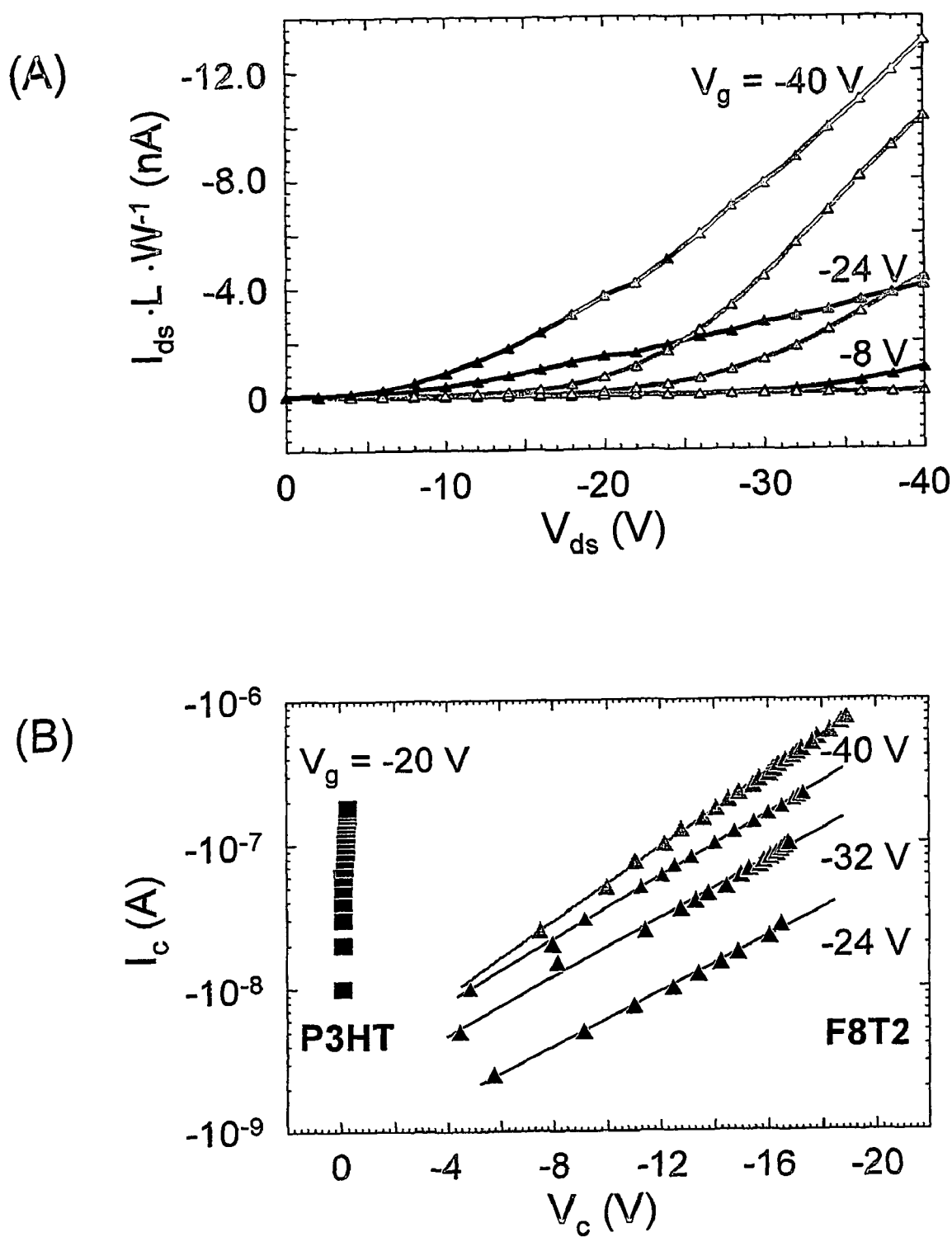
FIGS. 3A and 3B show channel length scaling analysis of embossed planar- and vertical-channel F8T2.

Remarkably, output and transfer characteristics of a representative vertical F8T2 FET fabricated with gold source (E1), drain (E2) and gate electrodes (FIG. 2A,B) show a clean field effect with operation in p-type accumulation mode. The ON-OFF current ratio of $10^3$ is reasonably high, even in the saturation regime ($V_{sd}$=−40V) where a high electric field is present in the pinch-off region near the drain electrode of this short channel device. In contrast to conventional planar F8T2 devices, the embossed vertical F8T2 FETs exhibit a superlinear dependence of the FET current on the source-drain bias, $V_{ds}$, without current saturation, also present, although to a lesser degree, in the planar embossed devices (FIG. 3A). This is caused by non-ohmic voltage drops across the embossed, charge-injecting F8T2/gold source-drain contacts. This is corroborated by the observation of higher ON-OFF current ratio when the top electrode E1 was the injecting source contact than when the bottom electrode E2 was the source.

In our experiments we focused on a narrow range of PVP thicknesses (0.5 to 1 μm), in which deposition and embossing conditions were optimized carefully. To quantify the contact resistance, analysis of channel length scaling was performed by comparing the normalized current $I^*_{ds}=I_{ds}\cdot L\cdot W^{-1}$ of embossed vertical-channel devices (L=0.7-1.2 μm) (grey lines in FIG. 3A) with that of embossed planar-channel devices (black lines) and of reference FETs in a conventional planar configuration (L=2-20 μm). At high source-drain voltages, clear scaling of the FET current with channel length is observed. The field-effect mobilities μ extracted from the saturated transfer characteristics of planar and vertical embossed as well as reference F8T2 devices are on the order of $2\text{-}3\cdot 10^{-3}$ cm$^2$V$^{-1}$s$^{-1}$. However, at small $V_{sd}$ the normalized current in short-channel vertical devices is significantly smaller than that of long-channel planar devices. From channel length scaling analysis, we extracted the current-voltage characteristics $I_c(V_c)$ of the parasitic source-drain contacts in series with the FET channel resistance. $I_c$ follows an exponential dependence $I_c=I_c^0\cdot e^{\alpha\cdot V_c}$ on the voltage $V_c$, dropping across the contacts with a pre-exponential factor $I_c^0$, and α≈0.25-0.3 (FIG. 3B). Similar behavior has been reported for the current-voltage characteristics in injection-limited hole-only polymer diodes. We conclude that at low $V_{sd}$, embossed F8T2 devices are injection limited. $I_c^0$ depends on gate voltage, indicating that the contact resistance is reduced by the applied gate voltage. The source-drain contact resistance might be associated with the small contact area between F8T2 and buried electrodes E2, E4 or with non-conformal coating of the semiconducting and dielectric polymers into the well. At the bottom of the groove the layers will most likely be thicker than at the top due to surface-tension and capillary-force effects during spin-coating. Atomic-force microscopy investigations of the topography of the grooves at various stages during the process (see e.g. FIG. 5C) have shown, however, that none of the deposited layers measurably planarizes the groove.

Figure 4:
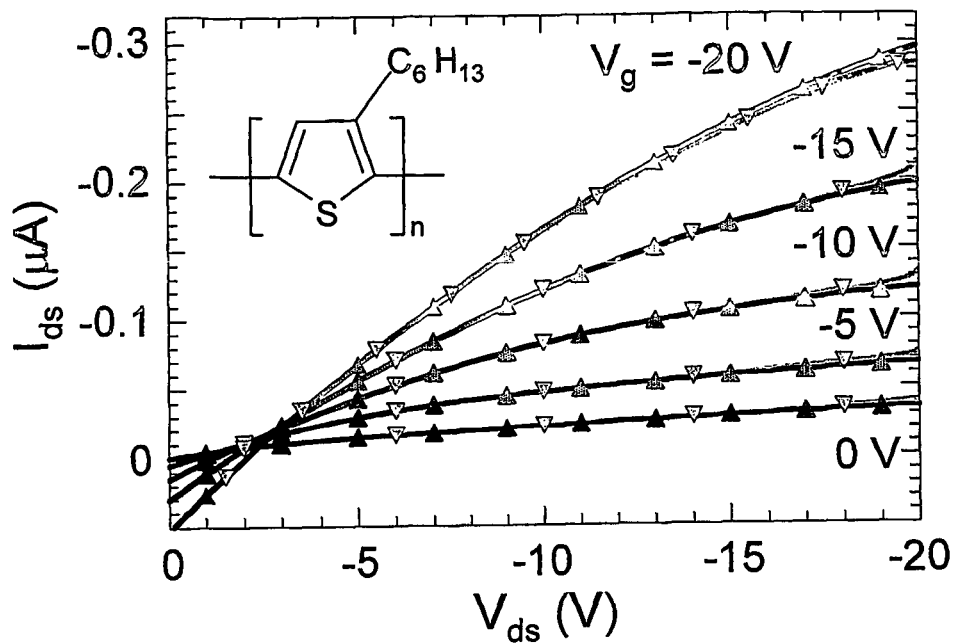
FIGS. 4A and 4B show output and transfer characteristics of an embossed vertical-channel FET with poly(3-hexylthiophene) (P3HT)
Figure 4:
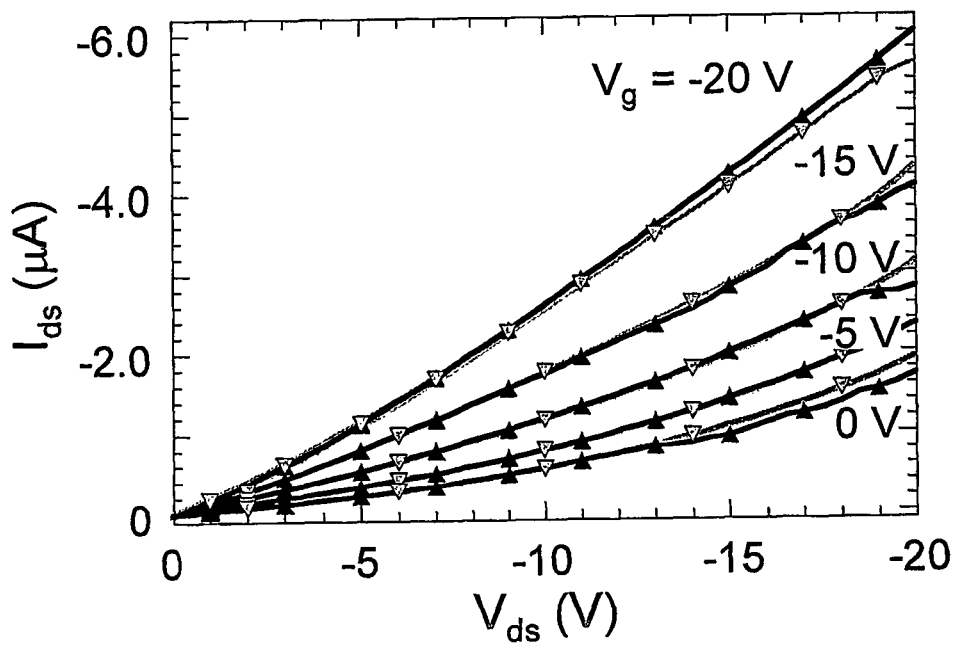

In order to reduce parasitic contact resistance, devices were also fabricated with P3HT as active material. The ionization potential of P3HT ($I_p$≈4.9 eV compared to $I_p$≈5.5 eV for F8T2) is well matched to the work function of gold/PEDOT. For planar embossed P3HT devices, current saturation is clearly observed (FIG. 4A). The non-linearities in the short-channel, vertical FET characteristics (FIG. 4B) can mostly be attributed to channel-length shortening effects, and to a lateral field-dependence of the field-effect mobility. The $I_c(V_c)$-characteristics for embossed P3HT devices shows that the contact-resistance is negligible (FIG. 3B, squares) and comparable to that of conventional planar P3HT devices. Therefore, contact resistance problems are not inherent to the embossing process but can, if desired, be addressed by suitable choice of polymer semiconductor. The mobilities extracted from the saturated transfer characteristics of both planar and vertical microcut, as well as reference P3HT devices are approximately 0.01 cm$^2$V$^{-1}$s$^{-1}$. Embossed P3HT devices exhibit stable and reproducible device characteristics. No hysteresis is observed between subsequent sweeps of the source-drain and gate voltage (FIG. 4). The relatively high OFF-currents at $V_g$=0 V observed for both the planar and the vertical device, are attributed to unintentional doping of the P3HT. This is typical also for conventional P3HT FETs in a top-gate configuration.

Structural characterization of the layers in the embossed grooves is challenging due to difficult preparation of electron microscopy cross-sections of polymer multilayers. However, we have succeeded in obtaining optical and environmental scanning electron micrographs (FIG. 1B,C) that clearly show that the microcutting process produces well-defined vertical sidewalls. Remarkably, no "smearing" of the top electrode along the indentation direction was observed. Unambiguous evidence for the integrity of the multilayer structure in the embossed grooves is obtained from electrical characterization: (a) The field-effect mobilities of planar and vertical-channel embossed devices with both F8T2 and P3HT are identical to those of reference devices fabricated in the same experiment using conventional planar lithographically define devices. Since the field-effect mobility is a very sensitive measure of the electronic structure and interface roughness at the semiconductor-dielectric interface, this is unambiguous evidence for the high structural quality of the active interface formed in the embossed grooves. (b) No electrical shorts between top and bottom electrodes are generated. After microcutting typical leakage currents between electrodes E1-E2 are on the order of 1 nA or less (PVP thickness of 0.7-1.2 μm, applied voltage of 40V), which is comparable to leakage currents between electrode E1 and E2 before the microcutting process. (c) The transistor current of embossed vertical channel P3HT devices with L=0.9 μm is higher by about one order of magnitude than that of P3HT reference devices fabricated in the same experiment using a conventional device configuration with L=10 μm, exactly, as expected from the reduction of channel length. The embossing method provides controlled, accurate definition of sub-micron critical feature size without degradation of polymer field-effect mobility, and results in significant enhancement of FET drive current capability.

Figure 5:
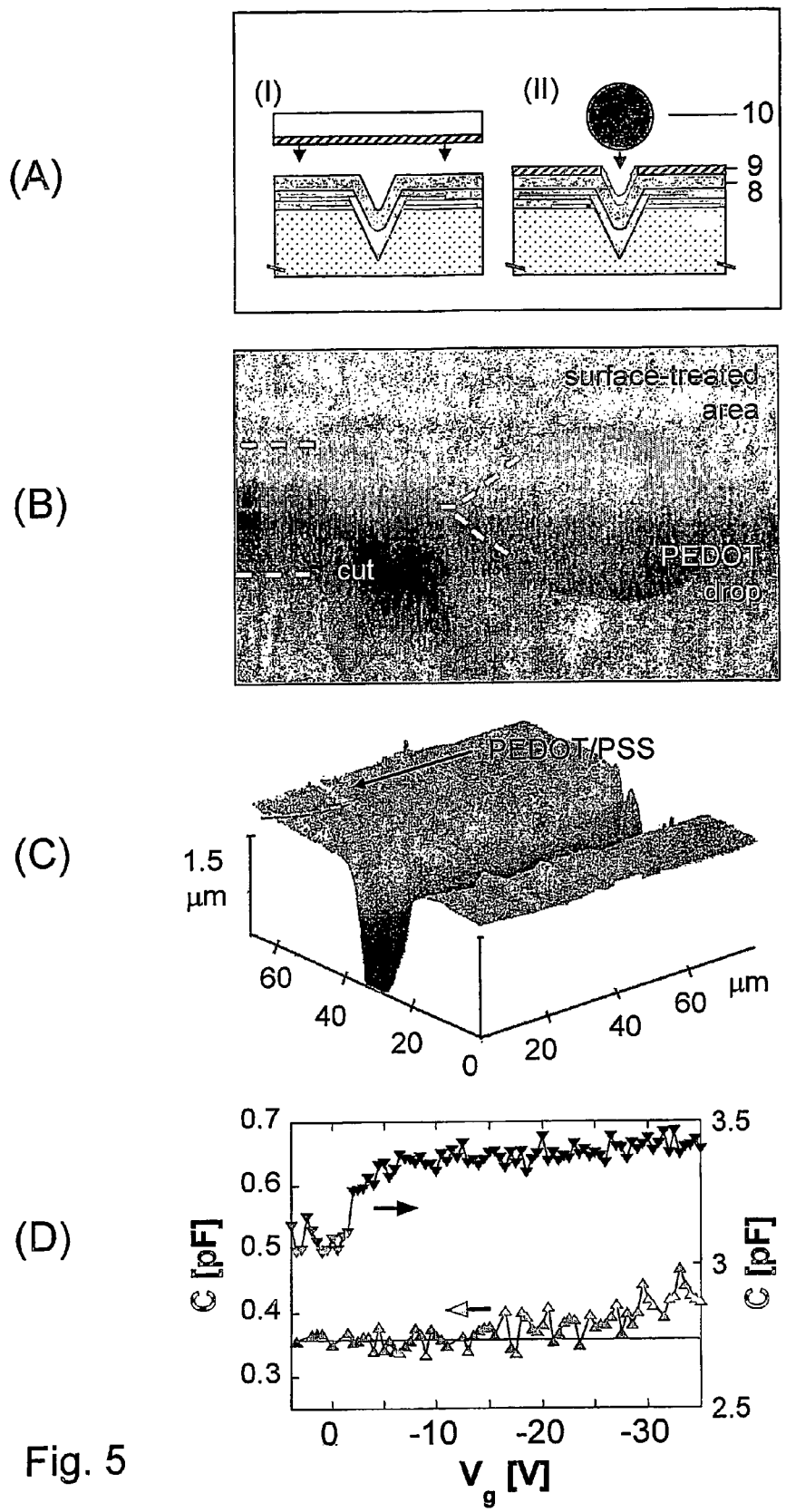
FIGS. 5A to 5D show formation of a self-aligned gate electrode inside the embossed FET channel.

To further increase transistor switching speed another important factor is the geometric overlap capacitance between the gate electrode and the source-drain electrodes. To reduce this capacitance, narrow gate lines that are self-aligned with the FET channel are required. To date, no approach for the self-alignment of the gate electrode of a printed polymer FET has, so far as the inventors are aware, been reported. Here we demonstrate a process for forming a printed self-aligned gate (FIG. 5A). After spin-coating the PMMA gate dielectric into the groove, the surface of the PMMA is rendered hydrophilic by a short, low-power oxygen plasma treatment. The substrate is then contacted with a flat, flexible stamp of poly(dimethyl siloxane) (PDMS) inked with a self-assembled monolayer of octyltrichlorosilane (OTS). The OTS is transferred onto the activated, hydrophilic PMMA only in the flat regions of the surface rendering those surface regions hydrophobic, while the PMMA surface inside the embossed grooves remains hydrophilic. This generates a surface-energy pattern used to direct-inkjet-printed droplets of PEDOT to flow into the groove, and confine the gate electrode to the narrow groove of width s=10-20 μm, which is self-aligned with the embossed source-and drain electrodes. When PEDOT droplets hit the surface in the vicinity of the grooves, they deform from a spherical into an oval shape (FIG. 5B) by combined surface-energy and capillary forces, which attract them to flow into the grooves. AFM microscopy showed no evidence for residual PEDOT in the flat regions of the surface (FIG. 5C). Control experiments with hydrophilic PMMA surfaces that had not been modified selectively with OTS have shown that on a wetting surface, capillary forces alone provide some, but less effective confinement of droplets. In this way we have fabricated operational planar and vertical embossed FETs with performance comparable to the ones described above. Capacitance-voltage (CV) measurements (FIG. 5D) show that the overlap capacitance per unit channel width of embossed planar devices with a self-aligned PEDOT/PSS gate (s=10-20 μm) is on the order of 0.3-0.5 pF/mm. This value is by one order of magnitude lower than the overlap capacitance of 3-4 pF/mm of a planar polymer FET with an unconfined inkjet printed PEDOT/PSS gate electrode of linewidth 60-80 μm.

We have shown that solid-state embossing combined with direct inkjet printing is a powerful manufacturing technique for solution-processed polymer FETs on flexible substrates. By direct-write printing electrodes, interconnects, active polymer islands and via-hole interconnects can be deposited. Embossing enables controlled definition of submicrometer critical features. Our method for surface energy-assisted confinement of printed electrodes in embossed grooves to reduce overlap capacitance can be applied more generally, for example, to define ink-repelling barriers that enable the accurate printing of source-drain electrodes with small channel lengths, or to reduce the linewidth of interconnect lines. Self-aligned, submicrometer vertical channels FETs with undegraded field-effect mobilities and reduced overlap capacitance will enable polymer integrated circuits with significantly improved switching speed.

Further down-scaling of L in the vertical-channel devices is possible. In our experiments the minimum channel length was limited only by leakage currents through the dielectric PVP spacer layer. These became significant for PVP thicknesses below 0.5 μm, but were present even prior to embossing. To solve this problem PET substrates with smaller surface roughness are required. For very short channel devices it will also become important to reduce frictional forces between the embossing master and the layers to be cut. Friction may force the top-layers downwards, along the indentation direction, but can be minimized by chemical modification of the master surface. Furthermore, selecting materials with $T_g \gg T_{emboss}$ will further prevent smearing and enhance the mechanical stability of the multilayer. Even in the planar device configuration further down-scaling can be realized, for example, by pressing the master into the multilayer only partially (e.g. using shorter embossing cycles and/or reducing the applied load) or by decreasing the height of wedges of the embossing master. For instance, using a master with a height h=1.5 μm, microwires of e.g. gold and PEDOT separated by less than 1 μm have been demonstrated previously.

A vertical-channel or planar-channel CHEMFET can be fabricated by the embossing process described above with the gate electrode exposed on the surface of the embossed microgroove. As a transduction mechanism a range of different mechanisms might be used, such as, but not limited to, analyte induced changes of the workfunction of the gate electrode, modification of the flat band voltage of the device by diffusion of species through the gate dielectric, or modifications of the resistivity of the gate electrode or the gate interconnect. The surface of the gate electrode might be modified in order to enhance the interaction with the analyte. In the case of a biosensor the surface of the gate electrode might be modified by deposition of a biomolecule, such as a DNA sequence or a protein, that exhibits a specific binding interaction with the species to be detected.

For the sensing action, the dependence of the work function of the conducting polymer gate electrode on pH can be exploited. Several techniques have been reported in the literature to enhance the sensitivity of polymer conductivity and/or work function on pH (see, for example, Janata et al., Nature Materials 2, 19 (2003), Shoji, et al., J. Am. Chem. Soc. 124, 12486 (2002), A. Talaie, Polymer 38, 1145 (1997)). Techniques to modify chemically the surface of the gate dielectric with thin films of ionisable polymers or with self-assembled monolayers that exhibit specific molecular recognition properties can also be used. A simple example of such surface functionalization are self-assembled monolayers comprising a carboxylic acid or other ionisable functional groups that can be used to shift flat band voltage of the transistor with pH. $H^+$ consuming or generating enzymes such as glucose oxidase, urease or penicillinase can be immobilised directly on the surface of the modified gates to create the corresponding metabolite sensors. Alternatively, the redox enzyme glucose oxidase is known to engage in direct electron transfer between the enzyme and the conducting polymer PEDOT/PSS that results in partial reduction of the PEDOT (Kros, et al., Adv. Mat. 2001, 13 (2001)) and can be used as a transduction mechanism.

The process of diffusion through the gate electrode may be enhanced by using a porous electrode. Porous electrodes can be fabricated from solution, for example by using a metallic ink containing small inorganic nanoparticles, such as colloidal silver. After deposition on the substrate the film of nanoparticles is annealed partially fusing the nanoparticles together. The degree of porosity can be controlled with the size of the nanoparticles, and the temperate at which the nanoparticles are fused. Ultrasmall nanoparticles can be fused at low temperature, because in a nanoparticle with a small diameter the melting point is reduced compared to a nanoparticle with a large diameter. In the case of conducting polymer gate electrode, porosity can be achieved by mixing a second component into the ink of the conducting polymer. The second component is preferably a polymer, that has a tendency to phase-separate with the conducting polymer. After deposition this second component is dissolved selectively by immersing the substrate in a solvent in which the conducting polymer itself is not soluble. An example of such a system is PEDOT/PSS mixed with PVP and deposited from a mixture in water and isopropanol (IPA). The PVP can be dissolved selectively, by dipping the substrate into IPA.

In another embodiment the gate electrode of the FET is omitted, and the transduction mechanism is based on the interaction of the fluid in the channel with the gate dielectric and/or its surface, which might, for example, affect the surface potential on the surface of the gate dielectric. The surface of the gate dielectric might be modified in order to enhance the interaction with the analyte. In the case of a biosensor the surface of the gate electrode might be modified by deposition of a protein, which exhibits a specific binding interaction with the species to be detected.

The fluid in the channel could be an electrolyte pumped through the microfluidic channel. In this case the gate voltage is controlled by the electrochemical potential of the electrolyte solution.

Figure 6:
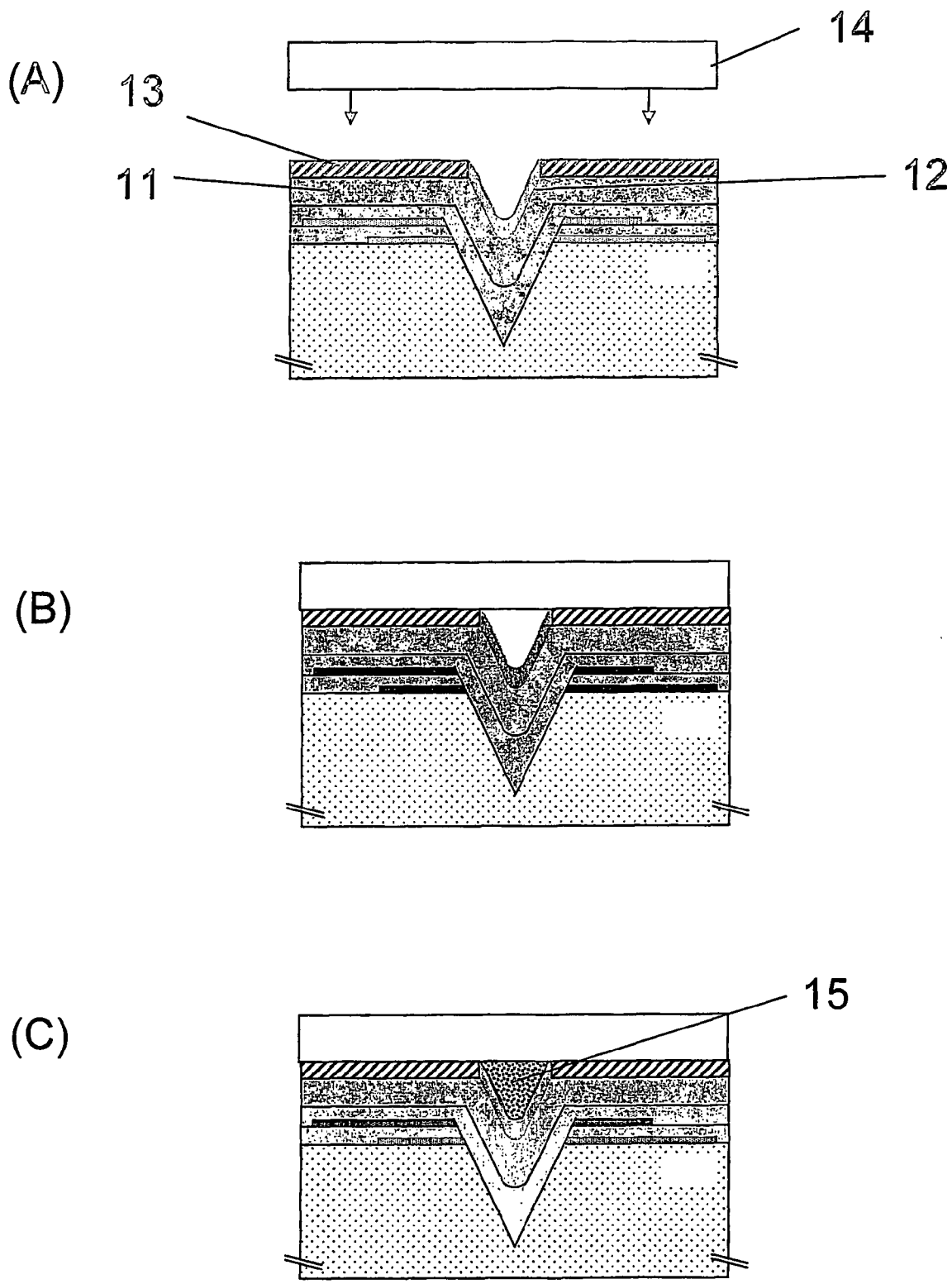
FIGS. 6A to 6C show a schematic diagram of a vertical-channel FET sensor integrated into a microfluidic channel according to one embodiment of the present invention.

We will now describe another important feature, i.e. the integration of the embossed electronic device into a microfluidic channel. After fabrication of the electronic device on a first substrate containing an array of embossed microgrooves, the substrate can brought in close contact with and bonded to a second substrate 14 (FIG. 6A). Preferably, the second substrate is a flexible substrate that is able to conform to the surface of the first substrate. An example of such a flexible substrate is an elastomer, such as for example PDMS. In order to establish a close contact, that provides a good seal against leakage of fluid or gas, pressure or heat might be applied during the bonding process. The surface of the first substrate 13, 12 might also have been treated prior to bringing it in contact with the second substrate, such as for example, exposure to an oxygen plasma in order to improve the bonding between the two substrates. Alternatively, either the first or second substrate might be coated with a lamination layer. One or both of the substrates maybe heated, preferably at or above the glass transition temperature of the lamination layer in order to form a tight seal between the two substrates. In this way a microfluidic channel is defined that can be used to control the flow of liquid 15 past the sensing device.

Other ways of integrating the device into a channel could be adopted. For example, the device could be formed on a flat substrate which could be adhered to a substrate that bears a microfluidic channel so that the device is exposed in the channel.

In preferred embodiments the second substrate can either be flat, as described above, or it may contain itself an array of microgrooves exposed at the surface that is to be married to the first substrate. Such microgrooves can be aligned with respect to the microgrooves in first substrates, or they might form an independent array of channels. The second substrate might contain channels that are used for opening or closing the channels on the first substrate, or to pump fluid or gas through the enclosed channels in the microgrooves of the first substrate. Valves and pumps can be formed by techniques, such as, but not limited to pneumatically actuated membranes (M. Unger, et al., Science 288, 113 (2000)).

According to one embodiment the second substrate can be chosen such as to provide efficient encapsulation of the sensor in the microgroove from the environment, such as preventing or inhibiting exposure of the sensor to oxygen or water. This is desirable in order to make the sensor less sensitive to unwanted variations of the characteristics caused by environmental factors, such as humidity, for example, that would be difficult to distinguish from the response to the species to be detected. A second substrate formed from PDMS provides protection and encapsulation against variations in humidity and oxygen concentration. It also reduces undesirable long term drift of the FET characteristics. The second substrate might also be coated with a dedicated encapsulation layer, such as a parylene coating, or a thin layer of an inorganic material such as $SiO_2$ or $SiN_x$. By using the second substrate both for the sealing of the flow channel and to provide device encapsulation, a simplification of the sensor manufacturing process can be achieved.

Figure 7:
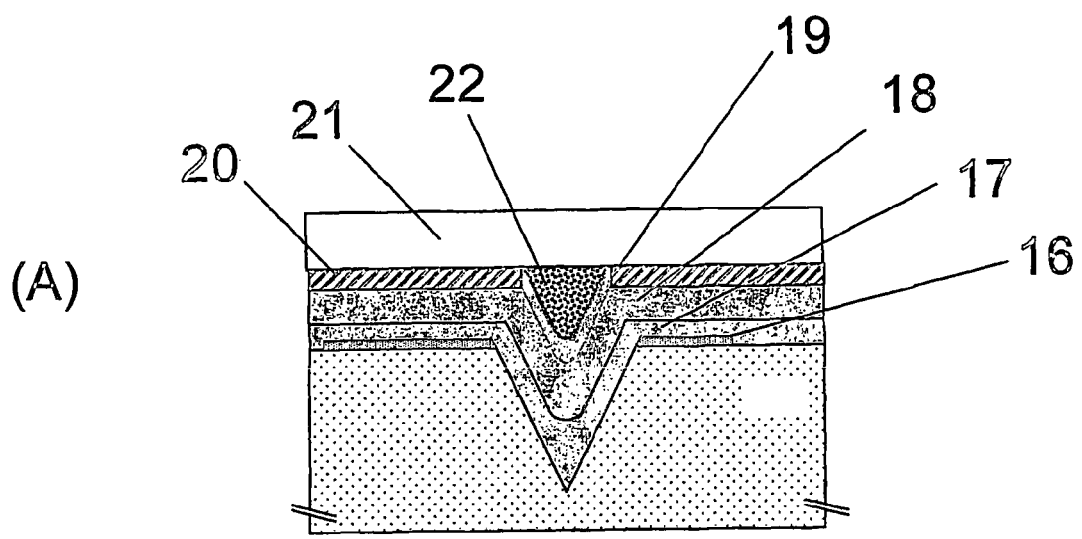
FIGS. 7A and 7B show other sensing devices integrated into a microfluidic channel.
Figure 7:
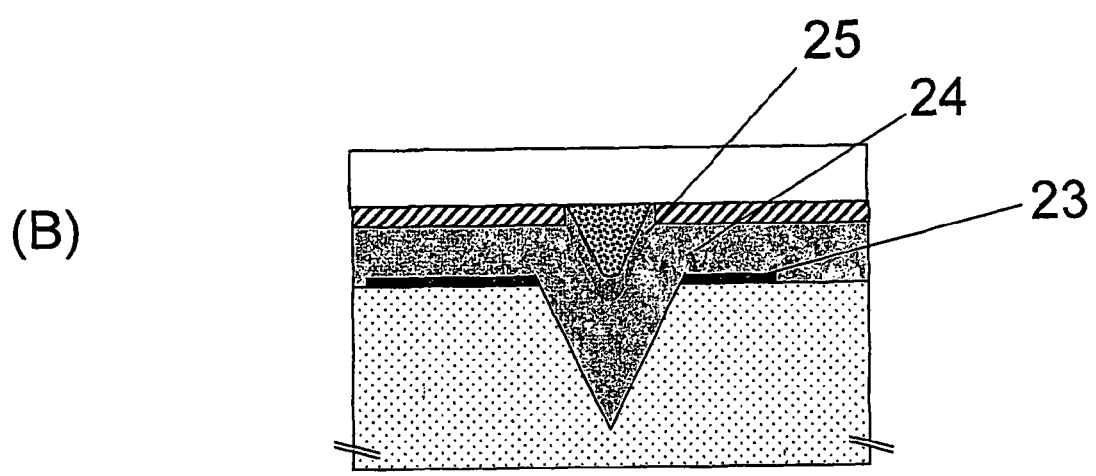

The device configuration for planar-channel (FIG. 7A) and vertical-channel FETs (FIG. 6) described above is one example of a configuration for an electronic device where the embossing step defines simultaneously a microgroove, and also defines a functional part of the electronic device (in this case the source and drain electrodes, and the self-aligned gate electrode). Other device configurations are possible. In the case of a simple chemical resistor (FIG. 7B) the embossing step can define the electrodes 23 in the same way as described above, followed by the simple deposition of a conductive or semiconductive material 24, the conductivity of which is sensitive to the presence of the analyte, into the groove. The surface 25 of such a conductive or semiconductive material might also be modified in order to enhance the selective interaction between the sensor material and the analyte. The FET described above might also be used a chemical capacitor by detecting shifts in the impedance/capacitance characteristics of the source/drain to gate junction.

The process of the manufacturing and the material of the microcutting tools that is used to emboss the microchannel on the first substrate is not critical, provided that these microcutting tools are sufficiently hard and capable of cutting through the layers. Critical is however that the height h of the features, exceeds the thickness d of the layer or layers that are to be cut. Characteristic dimensions of these features, such as the feature height h, preferably are in the range between 1 mm and 1 nm. More preferably these characteristic dimensions are between about 100 µm and 5 nm, and most preferably between 10 µm and 10 or 20 nm.

Also, it is crucial that the radius of curvature of the protruding edges of these features is preferably less than 500 nm, more preferably less than 100 nm, and most preferably less than 10 nm. The sharp protruding features may be of simple geometries (e.g. line-shaped ridges) or more complex such as interdigitated features. A microcutting tool according to the present invention comprises at least one cutting edge, but preferably a multitude of edges. The latter allows for fabrication of a multitude of devices in one single embossing/microcutting step. The protruding edges may all be of the same geometry or may differ from each other. For instance, a microcutting tool according to the present invention may comprise arrays of line-shaped edges with which for example pre-structured electrical-conductive layers on top of a polymeric substrate can be cut in one step leading to an array of electrodes e.g. for use in electrical devices such as thin-film transistors.

According to another embodiment the microcutting master could be either planar or cylinder-shaped or whatever geometry is best suited for the device and device configuration to be fabricated as well the fabrication process. Cylinder-shaped microcutting tools are particularly suitable as they allow for embossing of a continuous flexible substrate in a reel-to-reel process. Reel-to-reel fabrication offers higher throughput, and lower cost capability than a standard batch process. In this context it is of particular significance that the embossing is performed preferably in the solid state, in which the embossed grooves retain their shape after the embossing tool is retracted. If the embossing was performed in the liquid phase, it would be necessary to reduce the substrate temperature before removing the microcutting tool, which would be difficult to achieve with a rolling cylindrical microcutting tool.

Large-area microcutting tools according to one embodiment can be fabricated for instance by combining a multitude of microcutting tools comprising the same or different relief structures. Cylinder-shape microcutting tools may be fabricated by first producing a planar tool which is subsequently rolled or bended.

Suitable masters for use in processes according to the present invention can be made by a variety of methods known in the art, including, but not limited to anisotropic etching techniques, lithographic methods, electroplating, electroforming and the like. One method is to apply anisotropic etching techniques to fabricate suitable features, as these techniques can lead to features having edges of a radius of curvature of less than 10 nm in a most straight-forward way. In particular, anisotropic etching of single-crystalline or polycrystalline inorganic materials is possible. A most suitable material is, but the present invention is not limited to, single-crystalline {100} silicon, for which anisotropic etchants such as solutions of potassium hydroxide (KOH) or tetramethyl ammonium hydroxide (TMAH) in water, with or without the addition of isopropyl alcohol (IPA) can be used. Other materials different from {100} silicon and anisotropic etchants different from those listed above might be employed e.g. to vary e.g. etch angles or etching rate; these will be apparent to those ordinarily skilled in the art of microfabrication. Also, for fabricating more complex structures, such as rectangular-shaped corners needed for example for producing interdigitated features, anisotropic etching techniques incorporating different compensation structures might be applied which are designed such that corners are protected by a "sacrificial" beam or similar structure until the desired etch depth is reached. These etching-techniques are also well-known (cf. van Kampen, R. P. and Wolffenbuttel, R. F. *J. Micromech. Microeng.* 5, 91 (1995), Scheibe, C. and Obermeier, E. *J. Micromech. Microeng.* 5, 109 (1995), Enoksson, P. *J. Micromech. Microeng.* 7, 141 (1997)).

In a further embodiment microcutting tools are fabricated by first producing sharp features in e.g. a silicon waver by anisotropic etching techniques, from which subsequently replicas are made in materials such as thermoplastic and thermosetting polymers. This has the advantage that sharp grooves can be etched into the original master, e.g. a silicon waver, what is often a more straight-forward process than etching sharp ridges. The polymeric replicas of such an original master should be sufficiently hard and capable of cutting through the layers to be structured. Accordingly, polymers used for replica production preferably have a glass transition temperature larger than 25° C., more preferably larger than 110° C. and most preferably larger than 150° C. The latter temperatures generally are well known and can be found for instance in Polymer Handbook (Eds., J. Brandrup, H. Immergut, E. A. Grulke, John Wiley & Sons., New York, 1999). Preferably, high-glass transition, thermosetting resins are used for producing replicated microcutting tools, such as cyanate ester resins (e.g 4,4'ethylidenediphenyl dicyanate and oligo(e-methylen-1,5-phenylencyanate) or epoxy resins such as tetrafunctional tetraglycidyl diaminodiphenyl-methane). The latter may be mixed before with an aromatic hardener such as 4,4'-diamino diphenyl sulfone, DDS. In order to fabricate replicas, a polymer melt, solution or pre-polymeric liquid as those listed above is cast, injection- or reaction molded, and solidified in contact with the master structure by e.g. cooling, thermally or photochemically crosslinking. The original master surfaces may be rendered non-adhesive, e.g. by rendering it hydrophobic, using suitable surface treatments such as chemically modification with self-assembling monolayers (e.g. silylation from vapor phase using e.g. octadecyltrichlorosilane, perfluorodecyltrichlorosilane and allyltrimethqxysilane). Alternatively, release coatings or agents such as silicon oil may be employed.

Also, it will be apparent to those skilled in the art of microfabrication that such polymeric replicas of the original master structure again can be used to produce $2^{nd}$, $3^{rd}$ or higher generation replicas ("sub-masters") which have either the same relief structure as the original master or a negative of it. Crucial is that the final microcutting tool comprises sharp protruding edges, such as sharp ridges. In order to produce such "submasters" via e.g. embossing, injection- or reactive molding, which subsequently can be used to replicate the final microcutting tool, preferably polymeric materials are employed that display good non-adhesive properties, such as perfluorinated polymers, polyolefins, polystyrene, or silicone rubbers (e.g polydimethylsiloxane). Obviously, such sub-masters may be bended or rolled or shaped in whatever geometry is most desired depending on the device and device configuration to be fabricated in order to produce cylinder-shaped microcutting tools or microcutting tools of more complex geometries. For this purpose, it is a preferred feature of this invention that flexible, polymeric materials, such as polydimethylsiloxane or polyolefins are used for submaster production.

It is also possible to use microcutting tools fabricated by anisotropic etching directly from thin crystalline wafers. If the wafer thickness is less than 50 µm such microcutting tools are flexible and can be mounted on a cylindrical roller suitable for reel-to-reel embossing.

In order to fabricate complex integrated circuits using microcutting the the microcutting tool might be fabricated with an arbitrary pattern of wedges, that is able to define the critical device dimensions of an arbitrarily complex circuit. If such a complex master is defined by anisotropic etching of a crystalline wafer, sophisticated etching techniques such as corner compensation (cf. van Kampen, R. P. and Wolffenbuttel, R. F. *J. Micromech. Microeng.* 5, 91 (1995), Scheibe, C. and Obermeier, E. *J. Micromech. Microeng.* 5, 109 (1995), Enoksson, P. *J. Micromech. Microeng.* 7, 141 (1997)) need to be used in order to ensure that all protruding wedges of the tool that are supposed to cut a certain layer of the multilayer stack have the same height.

Alternatively, the microcutting tool may have a very simple wedge pattern, such as an array of parallel, linear wedges. In this case all critical device dimensions need to be layout on a regular grid. However, circuits of arbitrary complexity can still be defined by appropriately defining the coarse pattern of the layer to be cut, and by depositing appropriate interconnections between the regularly spaced devices. This process is particularly suited for a reel-to-reel process based on a combination of direct printing and microcutting. In a first step a regular array of source-drain electrodes with suitable interconnections are written by a technique such as inkjet printing. Then the channel gap between source-drain electrodes is defined by microcutting. An regular active matrix sensor array is an example where such a regular array of TFTs is particularly useful.

The wedges on the master may all have the same height or shape, or they may be of different shapes to emboss simultaneously features of different depth. The etching process to define the wedges of the master can be performed in subsequent steps to define several patterns of wedges with different heights, for example by varying the width of the lithographic features of the etch mask. Such a master is useful to define critical device dimensions in several layers of the device in a single embossing step.

The embossing step might be performed while the substrate or the surface layer of the substrate is in the solid state, near its glass transition, or in the liquid state.

The dimensions of the microfluidic channel can be varied over a large range depending on fluid volumes, as well as the fluid dynamical parameters of the fluid. In some cases, for example applications where living biological cells are passed through the microfluidic channel, the channel width and/or height may be on the order of 100 µm-1 mm. In order to enhance the sensitivity of the sensor to small concentrations of analyte to be detected the channel dimensions can be reduced in order to maximise the interaction of the analyte with the surface of the sensing device. Channel dimensions on the order of 10-100 µm, or even submicrometer dimensions can be achieved by standard microstructuring techniques.

The processes and devices described herein are not limited to devices fabricated with solution-processed polymers. Some of the conducting electrodes of the TFT and/or the interconnects in a circuit or display device (see below) may be formed from inorganic conductors, that can, for example, be deposited by printing of a colloidal suspension or by electroplating onto a pre-patterned substrate. In devices in which not all layers are to be deposited from solution one or more PEDOT/PSS portions of the device may be replaced with an insoluble conductive material such as a vacuum-deposited conductor.

For the semiconducting layer any solution processible conjugated polymeric or oligomeric material that exhibits adequate field-effect mobilities exceeding $10^{-3}$ cm$^2$/Vs, preferably exceeding $10^{-2}$ cm$^2$/Vs, may be used. Suitable materials are reviewed for example in H. E. Katz, J. Mater. Chem. 7, 369 (1997), or Z. Bao, Advanced Materials 12, 227 (2000). Other possibilities include small conjugated molecules with solubilising side chains (J. G. Laquindanum, et al., J. Am. Chem. Soc. 120, 664 (1998)), semiconducting organic-inorganic hybrid materials self-assembled from solution (C. R. Kagan, et al., Science 286, 946 (1999)), solution-deposited inorganic semiconductors such as CdSe nanoparticles (B. A. Ridley, et al., Science 286, 746 (1999)), or crystalline inorganic nanowires (X: Duan et al., *Adv. Mat* 12, 298-302 (2000)).

The electrodes may be coarse-patterned by techniques other than inkjet printing. Suitable techniques include soft lithographic printing (J. A. Rogers et al., Appl. Phys. Lett. 75, 1010 (1999); S. Brittain et al., Physics World May 1998, p. 31), screen printing (Z. Bao, et al., Chem. Mat. 9, 12999 (1997)), and photolithographic patterning (see WO 99/10939) or plating. Ink-jet printing is considered to be particularly suitable for large area patterning with good registration, in particular for flexible plastic substrates.

The device(s) can be deposited onto another substrate material, such as Perspex or a flexible, plastic substrate such as polyethersulphone. Such a material is preferably in the form of a sheet, is preferably of a polymer material, and may be transparent and/or flexible.

Although preferably all layers and components of the device and circuit are deposited and patterned by solution processing and printing techniques, one or more components such as a semiconducting layer may also be deposited by vacuum deposition techniques and/or patterned by a photolithographic process.

The sensing transducer devices according to the present invention may be part of a more complex circuit or device in which the sensing device is interfaced with other electronic devices, such as TFTs, capacitors, resistors, or diodes, such as light-emitting diodes, or photodiodes. These electronic functions might all be implemented on the same substrate. Electronic devices other than sensing transducers can be fabricated in the same way as the sensing transducers, i.e. by using embossing in order to define the critical device dimensions, in which case not all microchannels on the same substrate would be connected to the liquid flow system. Alternatively, any other fabrication technique for those devices known in the art may be used, including surface energy assisted inkjet printing, photolithographic patterning, gravure or screen printing. One configuration of integrating the sensor with other processing electronics is illustrated in FIG. 8(A). Conducting interconnects 27 are formed between the sensing elements integrated into the microfluidic channels, and electronic devices formed in separate regions of the substrate. These electronic devices might perform amplification of the small signal generated by the sensing device, such as in the case of an simple inverter amplifier (FIG. 8(B)), or other signal processing, such as storage of the information recorded by the sensor, or calibration of the sensor. The first substrate 26 is then laminated with a second substrate 32 in order to close the microfluidic channel as well as to provide encapsulation and protective functions for the electronic devices integrated onto the first substrate. The second substrate might also contain electronic devices which when brought into contact with the first substrate and aligned appropriately, make electrical contact with devices integrated onto the first substrate.

Figure 8:
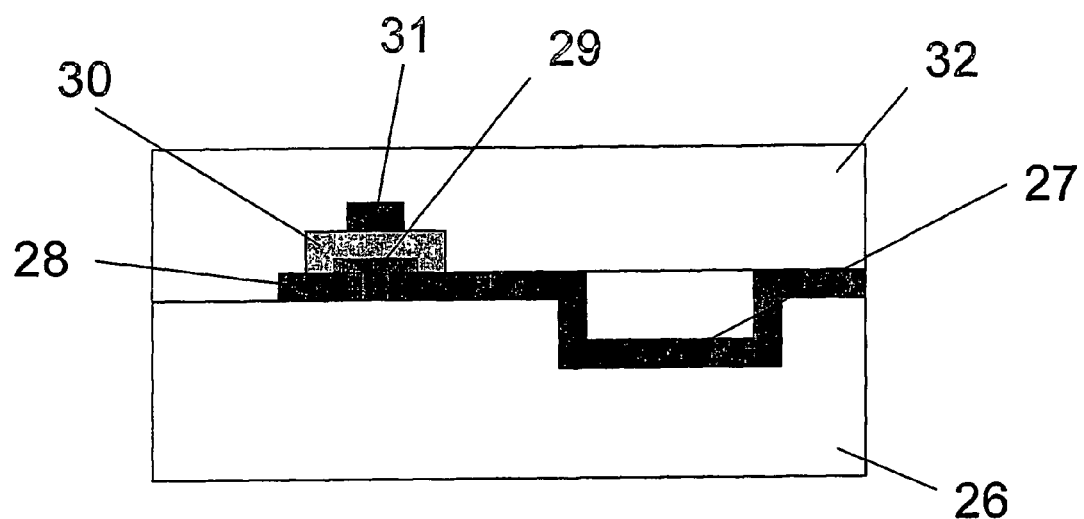
FIGS. 8A and 8B show an application of an embodiment of the present invention.
Figure 8:
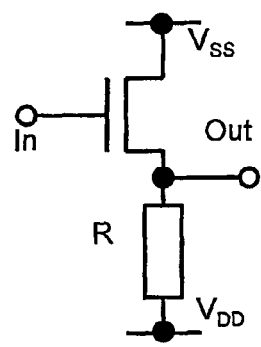

The present invention is not limited to the foregoing examples. Aspects of the present invention include all novel and/or inventive aspects of the concepts described herein and all novel and/or inventive combinations of the features described herein. For example, the microfluidic channels might be formed by techniques other than embossing, such as laser processing, or dry or wet etching. The sensing devices could be formed inside the channels by process steps that are separate from the process steps that form the microfluidic channel, for example, by solution-based direct-write deposition techniques, such as inkjet printing, or conventional manufacturing techniques based on photolithographic patterning and vacuum deposition. A direct-write technique such as inkjet printing is particularly suitable since it is capable of defining high resolution patterns on non-planar surfaces, i.e. is capable of defining the sensing devices inside the microfluidic channels, as well as the readout and amplification electronics that are integrated with a sensor (FIG. 8). An example of such a process would be the simultaneous definition of FET sensor on the bottom of a microfluidic channel with rectangular profile, the printing of interconnects on top of the vertical side walls of the channel interconnecting the sensor to printed devices in other regions of the substrate. The FET inside the channels can be formed for example by inkjet printing techniques such as described in (H. Sirringhaus, et al., UK 0009911.9).

The substrate onto which the electronic functionality and the sensing devices are integrated is preferably a flexible substrate, more preferably a flexible plastic substrate, such as a PET or a PEN substrate. The substrate might be of an environmentally friendly material, so as to be easily disposable or even biologically degradable.

The applicant draws attention to the fact that the present inventions may include any feature or combination of features disclosed herein either implicitly or explicitly or any generalisation thereof, without limitation to the scope of any definitions set out above. In view of the foregoing description it will be evident to a person skilled in the art that various modifications may be made within the scope of the inventions.

The invention claimed is:

1. A sensor comprising a first organic substrate having a microfluidic channel and an electronic sensing device located therein, and a second substrate bonded to the first substrate so as to close the microfluidic channel, wherein a conducting part of the electronic sensing device is exposed at the surface of the microfluidic channel, and said conducting part comprises poly(3,4-ethylenedioxythiophene) doped with poly(styrene sulphonic acid).

2. A sensor according to claim 1 for sensing the presence of glucose in the microfluidic channel.

3. A method comprising:
   defining in a single operation a microfluidic channel, and source and drain electrodes of a field-effect transistor,
   forming over the source and drain electrodes, an active semiconducting layer, a gate dielectric layer and a gate electrode,
   receiving a flow of liquid or gas in a portion of said microfluidic channel, and
   sensing a property of said liquid or gas.

4. A method as claimed in claim 3 wherein the said operation is embossing.

5. A method according to claim 3 wherein the microfluidic channel is located in an organic substrate.

6. A method according to claim 3 wherein current flowing between the source and drain electrodes is sensitive to environmental conditions within the channel.

7. A method according to claim 6 wherein the environmental conditions are temperature.

8. A method according to claim 6 wherein the environmental conditions are the presence of a species to be sensed.

9. A method as claimed in claim 3 wherein said field-effect transistor is a vertical-channel field-effect transistor.

10. A method comprising:
    forming a body comprising an electrically conductive layer;
    embossing the body to define in a single operation a microfluidic channel and source and drain electrodes of a field-effect transistor, the source and drain electrodes being exposed at the surface of the channel;
    forming over the source and drain electrodes, an active semiconducting layer, a dielectric layer and a gate electrode;
    receiving a flow of a liquid or gas in at least a portion of said channel; and
    sensing a property of said liquid or gas.

11. A method as claimed in claim 10 wherein defining said pair of electrodes comprises microcutting the electrically conductive layer.

12. A method as claimed in claim 10 further comprising depositing over the body a layer of a semiconductive material to form said active semiconducting layer.

13. A method as claimed in claim 12 further comprising depositing over the layer of semiconductive material a layer of an insulating material to form said gate dielectric layer.

14. A method as claimed in claim 13 further comprising depositing over the layer of insulating material a layer of a conductive material to form said gate electrode.

* * * * *